United States Patent
Grogan et al.

(10) Patent No.: US 11,950,768 B2
(45) Date of Patent: Apr. 9, 2024

(54) RADIALLY ADJUSTABLE SURGICAL DILATOR FOR REMOTE ACCESS SURGICAL PROCEDURES

(71) Applicant: Baylor College of Medicine, Houston, TX (US)

(72) Inventors: Raymon Grogan, Houston, TX (US); Stuart James Corr, Houston, TX (US); Alwin Mathew, Houston, TX (US); David Mitchell Moore, Houston, TX (US); Sandesh Reddy, Houston, TX (US); Mason Sheffield, Houston, TX (US); Fallon Wenck, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 43 days.

(21) Appl. No.: 17/450,789

(22) Filed: Oct. 13, 2021

(65) Prior Publication Data
US 2022/0110515 A1    Apr. 14, 2022

Related U.S. Application Data

(60) Provisional application No. 63/091,099, filed on Oct. 13, 2020.

(51) Int. Cl.
*A61B 1/32* (2006.01)
*A61B 1/01* (2006.01)

(52) U.S. Cl.
CPC . *A61B 1/32* (2013.01); *A61B 1/01* (2013.01)

(58) Field of Classification Search
CPC ......... A61B 1/32; A61B 1/01; A61B 17/0218; A61B 17/02; A61B 2017/32044; A61B 17/12104
USPC ........................... 600/201–245; 606/190–194
See application file for complete search history.

(56) References Cited

U.S. PATENT DOCUMENTS

| | | | |
|---|---|---|---|
| 1,267,066 A | 5/1918 | Flack | |
| 3,517,128 A | 6/1970 | Hines | |
| 5,454,365 A * | 10/1995 | Bonutti | A61B 17/0218 606/198 |
| 6,162,236 A * | 12/2000 | Osada | A61B 17/3439 606/191 |
| 8,435,174 B2 * | 5/2013 | Cropper | A61B 17/3421 600/203 |
| 10,595,899 B2 | 3/2020 | Bar et al. | |
| 2012/0022575 A1 | 1/2012 | Mire et al. | |
| 2014/0039264 A1 | 2/2014 | Heiman | |
| 2014/0277050 A1 | 9/2014 | Andreas et al. | |
| 2015/0342589 A1* | 12/2015 | Bootwala | A61B 5/24 600/208 |

\* cited by examiner

*Primary Examiner* — Eduardo C Robert
*Assistant Examiner* — Tara Rose E Carter
(74) *Attorney, Agent, or Firm* — Norton Rose Fulbright US LLP

(57) ABSTRACT

The present disclosure concerns systems and methods related to an adjustable surgical dilation device for the mechanical dilation of an anatomical opening, including, but not limited to, an endoscopic or robotic port. In specific embodiments, this device may create and expand an anatomical opening with a novel petal-like mechanism. In specific embodiments, this device may be utilized in laparoscopic procedures including, but not limited to, thyroid or parathyroid removal.

35 Claims, 11 Drawing Sheets

RADIALLY ADJUSTABLE SURGICAL DILATOR FOR REMOTE ACCESS SURGICAL PROCEDURES

This application claims priority to U.S. Provisional Patent Application Ser. No. 63/091,099, filed Oct. 13, 2020, which is incorporated by reference herein in its entirety.

TECHNICAL FIELD

The present disclosure is directed at least to the fields of surgery, medicine, and medical devices.

BACKGROUND

Endoscopic and robotic remote access approaches to the removal of thyroid or parathyroids are relatively new in the medical field. Traditionally thyroidectomy or parathyroidectomy involved cutting a large and invasive incision at the base of the neck where the thyroid or parathyroid is located, with the obvious result being a visible external/cutaneous scar. Newer endoscopic and robotic approaches to this operation offer a scarless or "hidden scar" alternative for patients who require thyroid removal and qualify for one of these surgical approaches (which is determined by acceptable thyroid size and health of the potential patient). The transoral vestibular approach is currently the only approach that leaves no visible scar on the outside of the patient's body. Other approaches move the scar from the neck to less visible locations. The initial incisions for these remote access thyroidectomy and parathyroidectomy procedures can be made in several areas including in the space between the bottom teeth and the lower lip (the oral vestibule) in the case of transoral endocrine surgery (TES). In this case, the path to the thyroid or parathyroid must go under the skin and along the curve of the chin and down towards the base of the neck. This path must be dilated to allow the surgical instruments to access the area. There is a range of dilation necessary (depending on the procedure being performed) along this path between 0.5 centimeters and approximately 2 centimeters in order to make enough room for placement of the endoscopic or robotic ports used to extract the thyroid or parathyroid.

After numerous successful transoral procedures were accomplished, it was found that the dilation portion of the procedure required high effort and time-intensive tactics from the surgeons because there is a thick band of tough connective along the chin and tissue in the neck which has proven difficult to penetrate and dilate. Penetration of this connective tissue using traditional surgical instruments increases the time of surgery and in some cases, increases the potential risk for the patients depending on the implemented dilation method. The dilation is currently accomplished by Hegar dilators, which are used for cervical dilation; Hegar dilators are rigid, slightly curved stainless steel rods of increasing thickness, and they are used in succession to dilate the track to an adequate size. This is a rather abrasive tactic which takes a great deal of time and effort from the surgeon, and it can also result in additional tissue damage from large forces inflicted with the blunt ends of a Hegar dilator. Other fixed size steel rod devices have been used with similar outcomes. Electrocauterization of the tissue and use of balloon catheters have also been explored for a potential solution to the dilation issue, but cauterization may cause damage of the overlying skin and other surrounding tissue (which has an abundance of nerve tissue, vocal chords, and delicate arteries) and balloon catheters cannot produce enough force to successfully dilate this tissue.

BRIEF SUMMARY

I. General Disclosures

The present disclosure is directed to a solution to the problems associated with current remote access surgical procedures including, but not limited to, endoscopic and robotic procedures. The present disclosure is particularly suited for use in endoscopic or robotic thyroid or parathyroid removal. Specifically, the present disclosure is directed to systems and methods for the creation and dilation of a surgical path, including, but not limited to, an endoscopic or robotic port. More specifically, this dilator is designed to create and expand the surgical path using a novel petal-like mechanism.

II. Systems of the Disclosure

The present disclosure is directed to systems for providing and expanding a remote surgical path using a novel petal-like mechanism. In specific embodiments, the device includes a dilator head positioned at the distal end of the device, including: an insertion tip positioned at the distal end of the dilator head, wherein the insertion tip is configured to create and/or expand a surgical path in an individual in need; and a dilator petal assembly positioned at the proximal end of the insertion tip, wherein the dilator petal assembly comprises two or more dilator petals; and a dilator body connected to the proximal end of the dilator head; wherein the device is configured to extend the dilator head in the closed state into the surgical path, wherein the device is configured to transition the dilator head into the open state by opening the dilator petal assembly radially outward from the dilator head, and wherein the device is configured to dilate the diameter of the surgical path by retracting the dilator head in the open state from the surgical path.

In specific embodiments, the insertion tip flares out from a conical point at the distal end of the insertion tip to a maximum diameter before tapering to a flat edge at the proximal end of the insertion tip. In specific embodiments, the maximum diameter of the insertion tip is about 5 mm.

In specific embodiments, the dilator head further includes: a movable, threaded internal bolt connected to the insertion tip, wherein the distal end of the internal bolt is attached to the proximal end of the insertion tip; and a stationary, internal threaded nut threaded onto a portion of the internal bolt, wherein the internal bolt is configured to rotate, and wherein the internal bolt is configured to move continuously distally or proximally through the nut based on the rotation of the internal bolt.

In specific embodiments, the dilator petal assembly is a hollow cylindrical assembly, wherein each of the two or more dilator petals is an equal, non-overlapping sector of the hollow cylindrical assembly, wherein the base of the hollow cylindrical assembly extends distally from the nut, and wherein the longitudinal axes of the two or more dilator petals are substantially parallel to the longitudinal axis of the dilator head when the dilator head is in the closed position. In specific embodiments, the proximal end of each dilator petal includes a thin, flexible tab, wherein the tab of each dilator petal is attached to the distal end of the nut, and wherein the dilator petal assembly is configured to bend or flex each dilator petal at the tab radially outward from the dilator head when the dilator head is in the open position. In specific embodiments, the distal end of the nut includes two or more slots, wherein the tab of each dilator petal is bonded inside of one of the slots by adhesive, welding, crimping, or other bonding method. In specific embodiments, the tab of each dilator petal is fastened to the distal end of the nut by a screw, a bolt, a rivet, or other mechanical fastener or bonded to the distal end of the nut by adhesive, welding, crimping, or other bonding method. In specific embodiments, each dilator petal includes a beveled edge angled toward the hollow cylindrical interior of the dilator petal assembly, wherein the beveled edges of the dilator petal assembly define a funnel-shaped cavity housing the insertion tip when the dilator head is in the closed position, wherein the hollow cylindrical interior of the dilator petal assembly houses a portion of the internal bolt, and wherein the cross-section of the interior of the hollow cylindrical interior of the dilator petal assembly is smaller than the cross-section of the insertion tip.

In specific embodiments, the proximal movement of the internal bolt through the nut is configured to force the insertion tip into the hollow cylindrical interior of the dilator petal assembly, and wherein the force of the insertion tip is configured to transition the dilator head into the open state by opening the dilator petal assembly radially outward from the dilator head based on bending or flexing of the two or more dilator petals at the tabs. In specific embodiments, the extent of the proximal movement of the internal bolt through the nut determines the dilation diameter of the dilator petal assembly, and wherein the dilation diameter of the dilator petal assembly determines the dilation diameter of the surgical path. In specific embodiments, the minimal diameter of dilation of the dilator petal assembly is about 5 millimeters, including when the dilator petal assembly is in a closed position. In specific embodiments, the maximal diameter of dilation of the dilator petal assembly is about 2 centimeters, including when the dilator petal assembly is in an open position.

In specific embodiments, the dilator head further comprises a stretchable sleeve comprising an interior cavity, wherein at least a portion of the dilator petal assembly is disposed within the interior cavity of the sleeve, and wherein the sleeve is configured to stretch to conform to the diameter of the dilator petal assembly when the dilator head is in the open position.

In specific embodiments, the dilator body includes: a guiding rod extending from the internal bolt, wherein the distal end of the guiding rod extends from the proximal end of the internal bolt, wherein the guiding rod is configured to rotate, and wherein the internal bolt is configured to rotate with the guiding rod; and an outer housing connected to the nut, wherein the distal end of the outer housing is attached to the proximal end of the nut, wherein the outer housing includes an inner cavity, and wherein the guiding rod is disposed within the inner cavity of the outer housing. In specific embodiments, the guiding rod is a hollow, cylindrical guiding rod or a solid cylindrical guiding rod comprising a proximal cavity. In specific embodiments, the guiding rod is a flexible guiding rod or an inflexible guiding rod. In specific embodiments, the guiding rod is a plastic guiding rod or a metallic guiding rod. In specific embodiments, the guiding rod is at least 10 inches in length. In specific embodiments, the outer housing is a cylindrical outer housing, and wherein the interior cavity of the outer housing is a cylindrical interior cavity. In specific embodiments, the outer housing is a flexible outer housing or an inflexible outer housing. In specific embodiments, the outer housing is a continuous outer housing or a segmented outer housing comprising uniformly-spaced rigid segments connected by intermediate flexible segments. In specific embodiments, the outer housing is a plastic outer housing or a metallic outer housing.

In specific embodiments, the device further includes: a guiding rod rotation system, wherein the distal end of the guiding rod rotation system is attached to the proximal end of the guiding rod, wherein the guiding rod rotation system is configured to rotate the guiding rod, and wherein the device is configured to dilate the dilator petal assembly by synchronous rotation of the guiding rod, and the internal bolt.

In specific embodiments, the device is configured to adjustably dilate the dilator petal assembly to a precise dilation diameter by adjusting the extent of synchronous rotation of the guiding rod, and the internal bolt.

In specific embodiments, the guiding rod rotation system comprises manual, mechanical, and/or electrical instrumentation configured to rotate the guiding rod.

In specific embodiments, a first section of the device comprising the dilator head and dilator body are reversibly attached to a second section of the device comprising the guiding rod rotation system, wherein, prior to surgical use, the first section of the device is configured to attach to the second section of the device, wherein, after surgical use, the first section of the device is configured to detach from the second section of the device, and wherein the attachment and detachment of the first section to and from the second section is based on the attachment and detachment of the guiding rod to and from the guiding rod rotation system.

In specific embodiments, the guiding rod rotation system includes: a planetary gear system, wherein the distal end of the planetary gear system can be attached to the proximal end of the guiding rod, wherein the planetary gear system is configured to rotate, and wherein the guiding rod is configured to rotate with the planetary gear system; a support base surrounding the planetary gear system; and a crank positioned at the proximal end of the body, wherein the distal end of the crank is connected to the proximal end of the planetary gear system, wherein the crank is configured to rotate, and wherein the planetary gear system is configured to rotate with the crank, wherein the device is configured to dilate the dilator petal assembly by synchronous rotation of the crank, the planetary gear system, the guiding rod, and the internal bolt.

In specific embodiments, the device is configured to adjustably dilate the dilator petal assembly to a precise dilation diameter by adjusting the extent of synchronous rotation of the crank, the planetary gear system, the guiding rod, and the internal bolt.

In specific embodiments, the planetary gear system includes: a central gear including a central gear shaft extending from the distal side of the central gear, wherein the central gear shaft is attached to the proximal end of the guiding rod, and wherein the central gear is configured to rotate the central gear shaft and the central gear shaft is configured to rotate the guiding rod; three planetary gears evenly-spaced around the central gear, wherein the teeth of the planetary gears are movably engaged with the teeth of the central gear, and wherein the planetary gears are configured to rotate the central gear; a stationary ring gear surrounding the planetary gears, wherein the teeth of the planetary gears are movably engaged with the teeth of the ring gear; and a carrier comprising carrier shafts extending from the carrier to the proximal side of the planetary gears, wherein the carrier is configured to rotate; wherein the carrier shafts are configured to rotate with the carrier, and wherein the carrier shafts are configured to rotate the planetary gears within the ring gear.

In specific embodiments, the central gear shaft is inserted into the proximal end of the hollow cylindrical guiding rod or into the proximal cavity of the solid cylindrical guiding rod.

In specific embodiments, a first section of the device comprising the dilator head and the dilator body is reversibly attached to a second section of the device comprising the planetary gear system and the crank, wherein, prior to surgical use, a first section of the device comprising is configured to attach to a second section of the device comprising the planetary gear system and the crank, wherein, after surgical use, the first section of the device is configured to detach from the second section of the device, and wherein the attachment and detachment of the first section to and from the second section is based on the attachment and detachment of the guiding rod to and from the central gear shaft.

In specific embodiments, the support base is connected to the outer perimeter of the ring gear.

In specific embodiments, the crank includes a crank handle at the proximal end of the crank and a crank shaft connected to the distal end of the crank handle, wherein the distal end of the crank shaft is connected to the proximal end of the carrier, wherein the crank handle is configured to rotate, wherein the crank shaft is configured to rotate with the crank handle, and wherein the carrier is configured to rotate with the crank shaft. In specific embodiments, the crank handle is a valve handle or a spoked wheel handle. In specific embodiments, the crank further includes a position indicator configured to indicate the precise dilation diameter of the dilator petal assembly based on the extent of rotation of the crank.

III. Methods of the Disclosure

The present disclosure is directed to methods for providing surgical access using a novel petal-like mechanism. In specific embodiments, the method includes the steps of: providing a device for dilation of a surgical path; wherein the device includes: a dilator head positioned at the distal end of the device, including: an insertion tip positioned at the distal end of the dilator head, and a dilator petal assembly positioned at the proximal end of the insertion tip, wherein the dilator petal assembly includes two or more dilator petals; and a dilator body connected to the proximal end of the dilator head; creating and/or expanding a surgical path in an individual in need using the insertion tip; extending the dilator head in the closed position into the surgical path; transitioning the dilator head into the open state by opening the dilator petal assembly radially outward from the dilator head; and dilating the diameter of the surgical path by retracting the dilator head in the open state from the surgical path.

In specific embodiments, the insertion tip flares out from a conical point at the distal end of the insertion tip to a maximum diameter before tapering to a flat edge at the proximal end of the insertion tip. In specific embodiments, the maximum diameter of the insertion tip is about 5 mm.

In specific embodiments, the dilator head further includes: a movable, threaded internal bolt connected to the insertion tip, wherein the distal end of the internal bolt is attached to the proximal end of the insertion tip; and a stationary, internal threaded nut threaded onto a portion of the internal bolt.

In specific embodiments, the dilator petal assembly is a hollow cylindrical assembly, wherein each of the two or more dilator petals is an equal, non-overlapping sector of the hollow cylindrical assembly, and wherein the base of the hollow cylindrical assembly extends distally from the nut, and wherein the longitudinal axes of the two or more dilator petals are substantially parallel to the longitudinal axis of the dilator head when the dilator head is in the closed position. In specific embodiments, the proximal end of each dilator petal includes a thin, flexible tab, wherein the tab of each dilator petal is attached to the distal end of the nut. In specific embodiments, the distal end of the nut includes two or more slots, wherein the tab of each dilator petal is bonded inside of one of the slots by adhesive, welding, crimping, or other bonding method. In specific embodiments, the tab of each dilator petal is fastened to the distal end of the nut by a screw, a bolt, a rivet, or other mechanical fastener or bonded to the distal end of the nut by adhesive, welding, crimping, or other bonding method.

In specific embodiments, each dilator petal includes a beveled edge angled toward the hollow cylindrical interior of the dilator petal assembly, wherein the beveled edges of the dilator petal assembly define a funnel-shaped cavity housing the insertion tip when the dilator head is in the closed position, wherein the hollow cylindrical interior of the dilator petal assembly houses a portion of the internal bolt, and wherein the cross-section of the interior of the hollow cylindrical interior of the dilator petal assembly is smaller than the cross-section of the insertion tip.

In specific embodiments, the step of opening the dilator petals radially outward from the dilator head includes the steps of: rotating the internal bolt; moving the internal bolt proximally through the nut based on the rotation of the internal bolt; forcing the insertion tip inside of the dilator petal assembly based on the proximal movement of the internal bolt through the nut; and bending or flexing the tabs of the dilator petals radially outward from the dilator head based on the force of the insertion tip.

In specific embodiments, the extent of the proximal movement of the internal bolt through the nut determines the dilation diameter of the dilator petal assembly, and wherein the dilation diameter of the dilator petal assembly determines the dilation diameter of the surgical path. In specific embodiments, the minimal diameter of dilation of the dilator petal assembly is about 5 millimeters, including when the dilator petal assembly is in a closed position. In specific embodiments, the maximal diameter of dilation of the dilator petal assembly is about 2 centimeters, including when the dilator petal assembly is in an open position.

In specific embodiments, the dilator head further comprises a stretchable sleeve comprising an interior cavity, wherein the dilator petal assembly is disposed within the interior cavity of the sleeve, and wherein the sleeve is configured to stretch to conform to the diameter of the dilator petal assembly.

In specific embodiments, the dilator body includes: a guiding rod extending from the internal bolt, wherein the distal end of the guiding rod extends from the proximal end of the internal bolt; and an outer housing connected to the nut, wherein the distal end of the outer housing is attached to the proximal end of the nut, wherein the outer housing includes an interior cavity, and wherein the guiding rod is disposed within the interior cavity of the outer housing, and wherein the step of rotating the internal bolt further comprises the steps of: rotating the guiding rod; and rotating the internal bolt with the guiding rod.

In specific embodiments, the guiding rod is a hollow, cylindrical guiding rod or a solid cylindrical guiding rod comprising a proximal cavity. In specific embodiments, the guiding rod is a flexible guiding rod or an inflexible guiding rod. In specific embodiments, the guiding rod is a plastic guiding rod or a metallic guiding rod. In specific embodiments, the guiding rod is at least 10 inches in length. In specific embodiments, the outer housing is a cylindrical outer housing, and wherein the interior cavity of the outer housing is a cylindrical interior cavity. In specific embodiments, the outer housing is a flexible outer housing or an inflexible outer housing. In specific embodiments, the outer housing is a continuous outer housing or a segmented outer housing comprising uniformly-spaced rigid segments connected by intermediate flexible segments. In specific embodiments, the outer housing is a plastic outer housing or a metallic outer housing.

In specific embodiments, the device further comprises a guiding rod rotation system, wherein the distal end of the guiding rod rotation system is attached to the proximal end of the guiding rod; wherein the step of rotating the guiding rod is accomplished by the guiding rod rotation system; and wherein the step of rotating the internal bolt comprises the step of synchronously rotating the guiding rod and the internal bolt.

In specific embodiments, the step of synchronously rotating the guiding rod and the internal bolt adjustably dilates the dilator petal assembly to a precise dilation diameter.

In specific embodiments, the guiding rod rotation system comprises manual, mechanical, and/or electrical instrumentation; and wherein the step of rotating the guiding rod is accomplished using the manual, mechanical, and/or electrical instrumentation.

In specific embodiments, the guiding rod is reversibly attached to the guiding rod rotation system; and wherein the method further comprises the steps of: prior to providing a device for dilation of a surgical path, attaching a first section of the device comprising the dilator head and the dilator body to a second section of the device comprising the guiding rod rotation system, wherein the attaching step is accomplished by attaching the guiding rod to the guiding rod rotation system; and, after retracting the dilator head in the open state from the surgical path, detaching the first section of the device from the second section of the device, wherein the detaching step is accomplished by detaching the guiding rod from the guiding rod rotation system.

In specific embodiments, the guiding rod rotation system includes: a planetary gear system, wherein the distal end of the planetary gear system is attached to the proximal end of the guiding rod; a support base surrounding the planetary gear system; and a crank positioned at the proximal end of the body, wherein the distal end of the crank is connected to the proximal end of the planetary gear system; wherein the step of rotating the guiding rod is accomplished by the steps of: rotating the planetary gear system; and rotating the guiding rod with the planetary gear system; wherein the step of rotating the planetary gear system is accomplished by the steps of: rotating the crank; and rotating the planetary gear system with the crank; and wherein the step of rotating the internal bolt comprises the step of synchronously rotating the crank, the planetary gear system, the guiding rod, and the internal bolt.

In specific embodiments, the step of synchronously rotating the crank, the planetary gear system, the guiding rod, and the internal bolt adjustably dilates the dilator petal assembly to a precise dilation diameter.

In specific embodiments, the planetary gear system includes: a central gear comprising a central gear shaft extending from the distal side of the central gear, wherein the central gear shaft is attached to the proximal end of the guiding rod; three planetary gears evenly-spaced around the central gear, wherein the teeth of the planetary gears are movably engaged with the teeth of the central gear; a stationary ring gear surrounding the planetary gears, wherein the teeth of the planetary gears are movably engaged with the teeth of the ring gear; and a carrier comprising carrier shafts extending from the carrier to the proximal side of the planetary gears; wherein the step of rotating the guiding rod comprises the steps of: rotating the central gear; and rotating the guiding rod with the central gear; wherein the step of rotating the central gear comprises the steps of: rotating the planetary gears; and rotating the central gear with the planetary gears; wherein the step of rotating the planetary gears comprises the steps of: rotating the carrier shafts; and rotating the planetary gears with the carrier shafts, wherein the step of rotating the carrier shafts comprises the steps of: rotating the carrier; and rotating the carrier shafts with the carrier; and wherein the step of synchronously rotating the planetary gear system includes the step of synchronously rotating the carrier, the carrier shafts, the planetary gears, the central gear, and the central gear shaft.

In specific embodiments, the central gear shaft is inserted into the proximal end of the hollow cylindrical guiding rod or into the proximal cavity of the solid cylindrical guiding rod.

In specific embodiments, the guiding rod is reversibly attached to the central gear shaft, and wherein the method further comprises the steps of: prior to providing a device for dilation of a surgical path, attaching a first section of the device comprising the dilator head and the dilator body to a second section of the device comprising the planetary gear system and the crank, wherein the attaching step is accomplished by attaching the guiding rod to the central gear shaft; and after retracting the dilator head in the open state from the surgical path, detaching the first section of the device from the second section of the device, wherein the detaching step is accomplished by detaching the guiding rod from the central gear shaft.

In specific embodiments, the support base is connected to the outer perimeter of the ring gear.

In specific embodiments, the crank includes: a crank handle at the proximal end of the crank; and a crank shaft connected to the distal end of the crank handle, wherein the distal end of the crank shaft is connected to the proximal end of the carrier, wherein the step of rotating the carrier comprises the steps of: rotating the crank shaft; and rotating the carrier with the crank shaft; wherein the step of rotating the crank shaft comprises the steps of: rotating the crank handle; and rotating the crank shaft with the crank handle; and wherein the step of rotating the crank further comprises the step of synchronously rotating the crank handle and the crank shaft.

In specific embodiments, the crank handle is a valve handle or a spoked wheel handle. In specific embodiments, the crank further comprises a position indicator, and the step of adjustably dilating the dilator petal assembly to a precise dilation diameter is achieved by synchronously rotating the crank, the planetary gear system, the guiding rod, and the internal bolt to an extent designated by the position indicator.

In specific embodiments, the surgical path traverses through the head or neck of the individual in need. In specific embodiments, the surgical path traverses through connective tissue. In specific embodiments, the surgical path traverses through epithelial tissue. In specific embodiments, the individual is in need of removal of one or more types of tissue. In specific embodiments, the individual in need is in need of removal of a parathyroid and/or thyroid. In specific embodiments, the surgical path for removal of the parathyroid and/or thyroid is created by inserting the device through the oral mucosa between the bottom lip and teeth of the individual in need.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawing, in which.

DETAILED DESCRIPTION

I. Definitions

Figure 1:
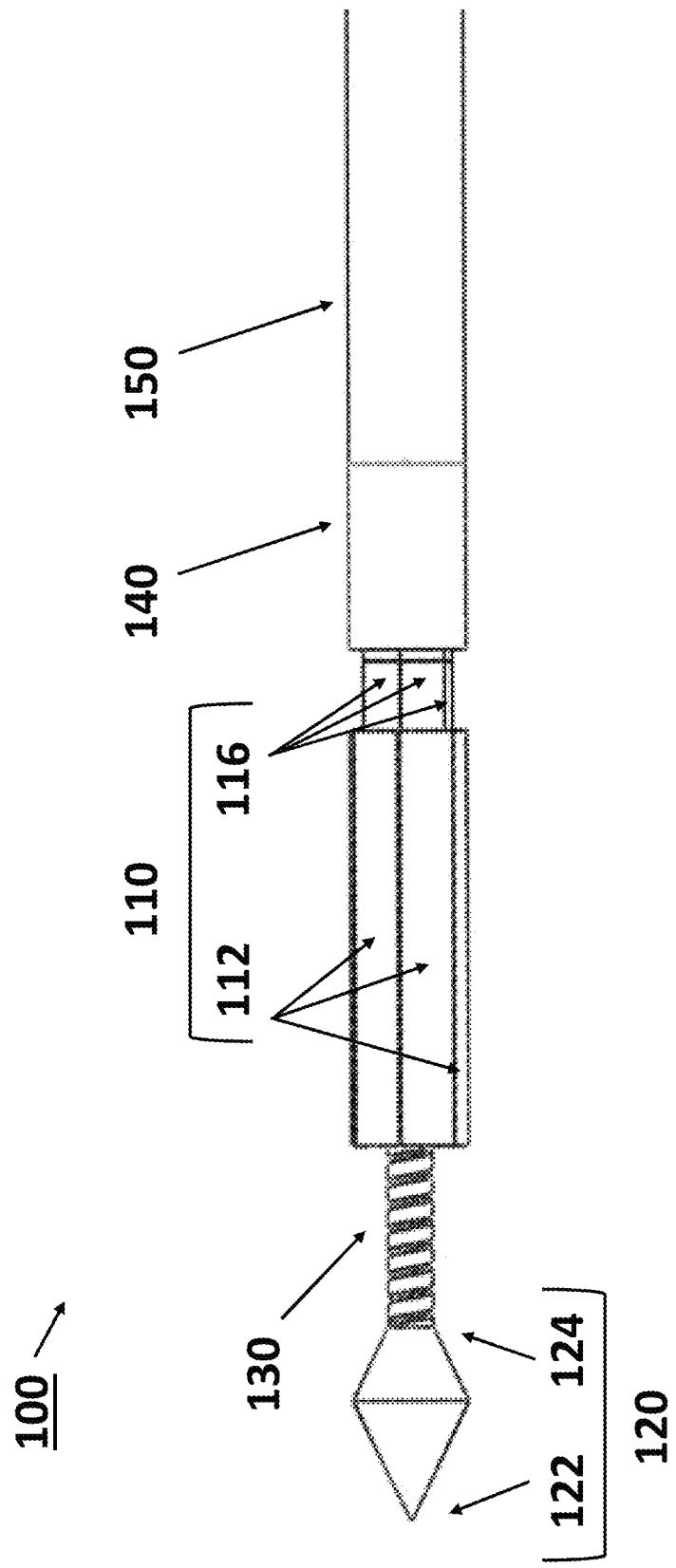
FIG. 1 illustrates an external side view of one embodiment of the distal end of the device including the dilator head and body with the dilator petal assembly in the closed position.

As used herein, the terms 'proximal' and 'distal' are used with reference to an operator (e.g., doctor, nurse, technician) such that a proximal side refers to the side closer to the operator and a distal side refers to the side away from the operator. For example, a blade end of a knife used by a surgeon to create an incision in a patient's body is the distal end, while a handle end held by the doctor would be the proximal end.

As used herein, the term "hollow cylindrical configuration" refers to an cylinder with a hollow cylindrical channel, also known as an open cylinder, coaxial cylinder, or hollow tube.

As used herein, the term "diameter of dilation" refers to the diameter of a circle defined by the tips of the dilator petal assembly in the open position.

II. General Embodiments

Embodiments of the disclosure include systems and methods useful for the mechanical dilation of a surgical path. In specific embodiments, the surgical path is a central laparoscopic port created and utilized during thyroid or parathyroid removal. In specific embodiments, a device may create and/or be inserted into an initial surgical path while in the closed state and then the device may be opened to dilate the surrounding tissue into the desired diameter. In specific embodiments, the device may be retracted from the initial surgical path while in the expanded state to dilate the surgical path as the device passes back out of the tissue.

There are multiple areas of the body that may benefit from dilation of a surgical path by such a device. The device is designed so that it is agnostic to tissue type, thus the device may be used to create, expand, and/or dilate any bodily organ or tissue that requires dilation. Non-limiting examples of specific tissues and organs include: any luminal organ and their junctions such as the esophagus, stomach, duodenum, small intestine, large intestine, rectum or anus; blood vessels such as peripheral veins and arteries, central veins and arteries, or coronary veins and arteries; genitourinary organs and tissues such as the ureters, bladder, and urethra; fascia and fascial planes such as the chin or neck fascia and fascial planes, abdominal wall fascia and fascial planes, fascia and fascial planes of the extremities; and skin, soft tissue, muscle, and subcutaneous tissue such as the tissues of the neck, abdominal wall, chest wall or limbs.

The dilator body may be long and narrow as well as flexible in order to be capable of exerting large, consistently applied forces to assist and improve a laparoscopic surgical procedure. The device, when closed, may have a maximum radius of 5 millimeters (an adequate size for insertion). The device, when open, may be capable of radial dilation of equal to or greater than 5 millimeters. In a specific embodiment, the device, when open, may be capable of radial dilation up to 2 centimeters (the maximum dilation needed in order to extract a thyroid within the surgery's acceptable parameters). The device may employ rotational force from a crank (rotated by a surgeon) converted to radial dilation of a small dilator petal assembly at the distal end of the dilator device.

In specific embodiments, the device may create and widen a central port from 5 millimeter to 20 millimeter in diameter for use during thyroid or parathyroid removal. In specific embodiments, the device may utilize a sharp insertion tip to create a laparoscopic port. In specific embodiments, the insertion tip may penetrate and expand the tough, thick connective tissue found underneath the chin for use during thyroid or parathyroid removal. In specific embodiments, the device may widen a laparoscopic port by radial expansion of a dilator petal assembly positioned in proximity to the insertion tip. In specific embodiments, the device may employ a manual hand crank to adjust the radial expansion of the dilator petal assembly to control the diameter of the laparoscopic port. In specific embodiments, the device may be retracted from the laparoscopic port while the dilator petal assembly is in the open position to dilate the entire length of the surgical path.

The device may have an insertion tip with a sharp rigid point at the distal end for precise and easy insertion into tissue. The insertion tip point allows for improved track formation with minimal physician force required. The proximal end of the insertion tip may taper to a flat edge to create smooth expansion of the device and to aid with backward movement of the dilator and avoid catching on tissue. The insertion tip may be at the distal end of a small threaded internal bolt. The insertion tip may be up to approximately 5 mm in diameter and approximately up to one inch in length. The insertion tip and internal bolt may be produced as one piece of metal, such as stainless steel, which can experience and exert forces of significant magnitudes, as they are made of one piece of continuous metal. This great force assists the device in penetrating and radially tearing through the tissue, such as the chin fascia, and using a metal, such as steel, internal bolt as the core of the dilation head provides stability and lowers the potential for mechanical failure.

The internal bolt may rotate proximally through a nut as an external crank is manually turned. The proximal movement of the internal bolt and insertion tip may radially dilate a dilator petal assembly including at least two dilator petals that may open to the desired dilation diameter chosen by the surgeon. In some embodiments, the dilator petals are designed to reduce unnecessary gaps in the design that could lead to increased tissue trauma and insufficient dilation. In some embodiments, the petals are produced as individual, separate pieces and are later formed into a hollow cylindrical dilator petal assembly that extends distally from the nut.

Tabs at the base ends of the dilator petals may be anchored in the distal end of a firm, slender nut that may keep them in place and may allow for strong mechanical force to be exerted and experienced by the device. When the dilator petal assembly is in the closed position, the dilator petal tips may allow the dilator petal assembly to sit in line with the insertion tip while the tabs sit in line with the nut. This may assist in proper track formation and maintaining a minimum dilation diameter. The tabs may be attached to the nut by adhesives, welding, crimping, or other bonding methods or by mechanical fasteners including a screw, a bolt, a rivet, a weld, or a hinge. For example, a hole may be tapped through the tabs and the nut and a pin may be used to secure the tabs to the nut to firmly secure the dilator petals to the rest of the design. Alternately, the tabs may be inserted into slots made in the nut and various adhesive, welding, crimping, or other bonding methods may be used to secure the tabs within the slots to firmly secure the dilator petals to the rest of the design. In addition to securing the dilator petals to the nut, the tabs also may allow for increased flexibility and allows the dilator assembly petals to bend or flex, resulting in the outward expansion utilized by the device to dilate a surgical opening.

The dilator petal assembly may be covered by a stretchable sleeve configured to stretch to conform to the diameter of the dilator petal assembly. In some embodiments, the sleeve will minimize possible tissue damage from the pronounced edges of the dilator petals and will distribute the force of dilation across the gaps between the dilator petals as the dilator petal assembly radially expands. The stretchable sleeve may also maintain maximum sterility of the device, encouraging a more radial/circular dilated tract shape, discouraging friction between the tissue and device, and preventing lodging or loss of device parts in the patient during use.

The sleeve may have an open cylindrical shape when the dilator petal assembly is closed and may expand into an umbrella-like shape as the dilator petal assembly opens. The sleeve may cover the outside of the dilator petal assembly and the tips of the dilator petals, but the conical insertion tip will not be encased. The sleeve may be anchored to the proximal end of the dilator petal assembly and anchored to the tips of the dilator petals. Possible anchoring methods include mechanical anchoring (divots or notches in the anchor points, for example), fusion by melting, or any other desired adhesion method with supplement of glue/fixative adhesion.

The sleeve may be constructed of a flexible/elastic plastic or polymer. The sleeve may be a disposable sleeve. The disposable sleeve may be attachable and detachable to and from the dilator petal assembly such that a fresh sleeve may be attached to the device prior to a surgical procedure and detached and disposed of after a surgical procedure.

The proximal end of the internal bolt may be firmly adhered to a the distal end of a guiding rod. The guiding rod may compose the majority of the device's length. The guiding rod may be flexible or inflexible. The guiding rod may be a hollow cylindrical guiding rod or a solid cylindrical guiding rod comprising a proximal cavity. The guiding rod may be a plastic or metallic guiding rod. The guiding rod may be at least 10 inches in length. The guiding rod may be encased in an outer housing. The outer housing may be flexible or inflexible. The outer housing may be a plastic or a metallic outer housing. The outer housing may be continuous or segmented. The outer housing may be flexible to allow for bending around the extreme curvature of the chin of the patient, which competing Hegar dilators lack substantially. Hegar dilators are completely rigid with a subtle, fixed curve in the stainless steel body, and they are difficult to maneuver properly through the surgical track for laparoscopic thyroidectomies. A flexible guiding rod and a flexible outer housing will allow for greatly increased precision and range of motion within the site of surgery, which minimizes the tissue damage often seen with electrocauterization methods of tissue dilation. The hollow space allows rotation of the movable, external threaded internal bolt proximally through the stationary, internal threaded nut, achieving dilation of the dilator petal assembly while simultaneously keeping the rest of the distal end of the device stationary. This design will help reduce trauma to surrounding tissue and decrease risk for the patient.

In specific embodiments, the proximal end of the guiding rod is firmly adhered to a guiding rod rotation system. In specific embodiments, the guiding rod rotation system applies rotational force to the guiding rod, causing the guiding rod to rotate. The guiding rod rotation system may employ manual, mechanical, and/or electrical instrumentation to rotate the guiding rod, such as manual rotation, rotation generated by a connected gear system, rotation generated by a connected motor, or any means capable of causing the guiding rod to rotate. The rotational force may be clockwise in relation to the assumption that the dilator tip is pointed away from the reference point, i.e., the viewer is pointing the dilator so that the base of the dilator head is facing them. In such embodiments, turning counterclockwise will result in the petals contracting inwards toward the tip if previously opened to any radial dilation.

In specific embodiments, the guiding rod rotation system may comprise a planetary gear system and a crank. In order to reduce the speed of dilation when compared to currently used methods, a planetary gear system may be added in the design to increase the rotational velocity of the threads of the internal bolt and therefore radial dilation of the petal assembly. All included gears may be produced with metal, such as steel or with plastic, such as rigid, smooth plastic.

The central gear shaft of the central gear may be inserted into the proximal end of the hollow cylindrical guiding rod or the proximal cavity of the solid guiding rod. The section of the device comprising the dilator head and the dilator body may be attached and detached from the section of the device comprising the gear and crank before and after surgical use by attaching and detaching the proximal end of the guiding rod from the central gear shaft. The section of the device comprising the dilator head and the dilator body may be readily disposable and may be replaced after each surgical use. The section of the device comprising the gear and crank may be reusable and may be readily sterilized after each surgical use. Further, the device may be packaged, shipped, and stored as a single section in which the disposable and reusable sections are attached or the unattached disposable and reusable sections of the device may be packaged, shipped, and stored separately.

The device may include a planetary gear system in order to significantly increase the ratio of rotational velocities of the dilator internal bolt and the crank handle, respectively. This in turn reduces the exertion force, the number of crank rotations, and time spent by the surgeon using the device. The central gear may be turned and orbited by three planetary gears, which are fixed in a larger inverted gear. To allow for increased range of motion and stability, a handheld support base may surround the planetary gear system. The planetary gear support base may be a rounded square, which can easily be held and gripped tightly by the surgeon while rotating the crank handle. Making the planetary gear system and crank handheld increases the maneuverability of the dilator while also eliminating the need for a surgical stand or table to be used for this device. The crank itself may be larger to increase the control the user/surgeon has in making minute adjustments to the dilation size or applying a decent amount of force to the crank handle. The crank shaft may be thick and solid to decrease the potential for mechanical failure of the crank during rotation. The crank is adhered at its base to the crank shaft, which attaches the crank to the planetary gear rotator.

The handle may be a three-pronged handle. The distal end of this handle may be the crank shaft, which may be easily controlled by the surgeon and which may be enveloped in the body of the crank. The crank may have a position indicator which notifies the surgeon of the precise diameter of the expanded petal as the crank is rotated.

In specific embodiments, the surgical path is made through an epithelial layer, such as the oral mucosa in transoral endocrine surgery (TES), of the individual in need. In specific embodiments, the surgical track is made through connective tissue, such as the chin fascia in TES. In specific embodiments, the individual is in need of repair or removal of one or more types of tissue, such as the removal of a diseased parathyroid and/or thyroid in TES.

III. Systems of the Disclosure

Embodiments of the disclosure include systems and methods useful for the mechanical dilation of a surgical path. Turning to the figures, FIG. 1 illustrates an external view of one embodiment of the distal end of the device 100 with the dilator petal assembly 110 in the closed position. The insertion tip 120 is positioned at the distal end of the device 100 to allow for the creation of the surgical path. The insertion tip 120 flares out from a conical, rigid insertion tip point 122 at the distal end of the insertion tip to a maximum diameter before reverse-tapering to a flat insertion tip base 124 at the proximal end of the insertion tip. The insertion tip base 124 is directly connected to the movable, external threaded internal bolt 130. The insertion tip base 124 is attached to the distal end of internal bolt 130. For illustrative purposes, the internal bolt 130 is shown in an extended position such that the threads of internal bolt 130 are visible past the dilator petal assembly 110. In some embodiments, the internal bolt 130 never extends past the dilator petal assembly 110. A portion of the internal bolt 130 is threaded within the stationary, internal threaded nut 140. The proximal end of the dilator petal assembly 110 is attached to the distal end of the nut 140. In the closed position, the dilator petal assembly 110 is comprised of individual dilator petals 112 arranged in a hollow cylindrical assembly extending distally from the nut 140. The dilator petals 112 each have a tab 116 at the proximal end through which each dilator petal 112 is attached to the distal end of the nut 140. An outer housing 150 is attached to the dilator head at the proximal end of the nut 140.

Figure 2:
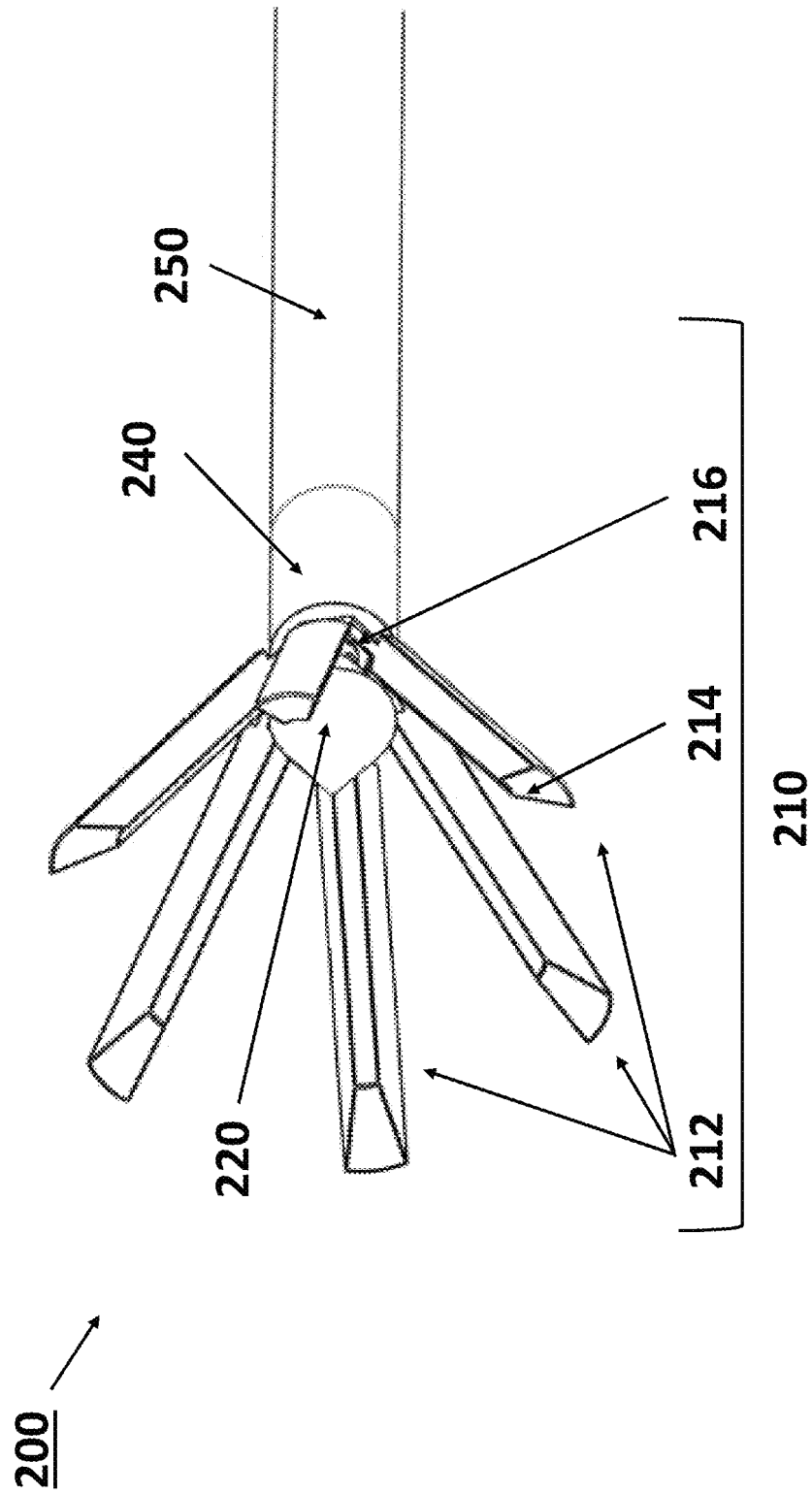
FIG. 2 illustrates an external perspective view of one embodiment of the distal end of the device including the dilator head and body with the dilator petal assembly in the open position.

FIG. 2 illustrates an external view of one embodiment of the distal end of the device 200 with the dilator petal assembly 210 in the open position. The maximum diameter of the insertion tip 220 is greater than the inner diameter of the closed dilator petal assembly 210. To achieve the open position, rotation of the movable, external threaded internal bolt (not shown) proximally through the stationary, internal threaded nut 240 forces the insertion tip 220 into the interior of the dilator petal assembly 210, which spreads the dilator petals 212 radially outward by bending or flexing the tabs 216 away from the insertion tip 220. With the dilator petal assembly 210 in the fully open position, the dilator petal tips 214 are spread radially outward from the nut 240 to a precise maximum dilation diameter. The outer housing 250 is attached to the device 200 at the proximal side of the nut 240.

Figure 3:
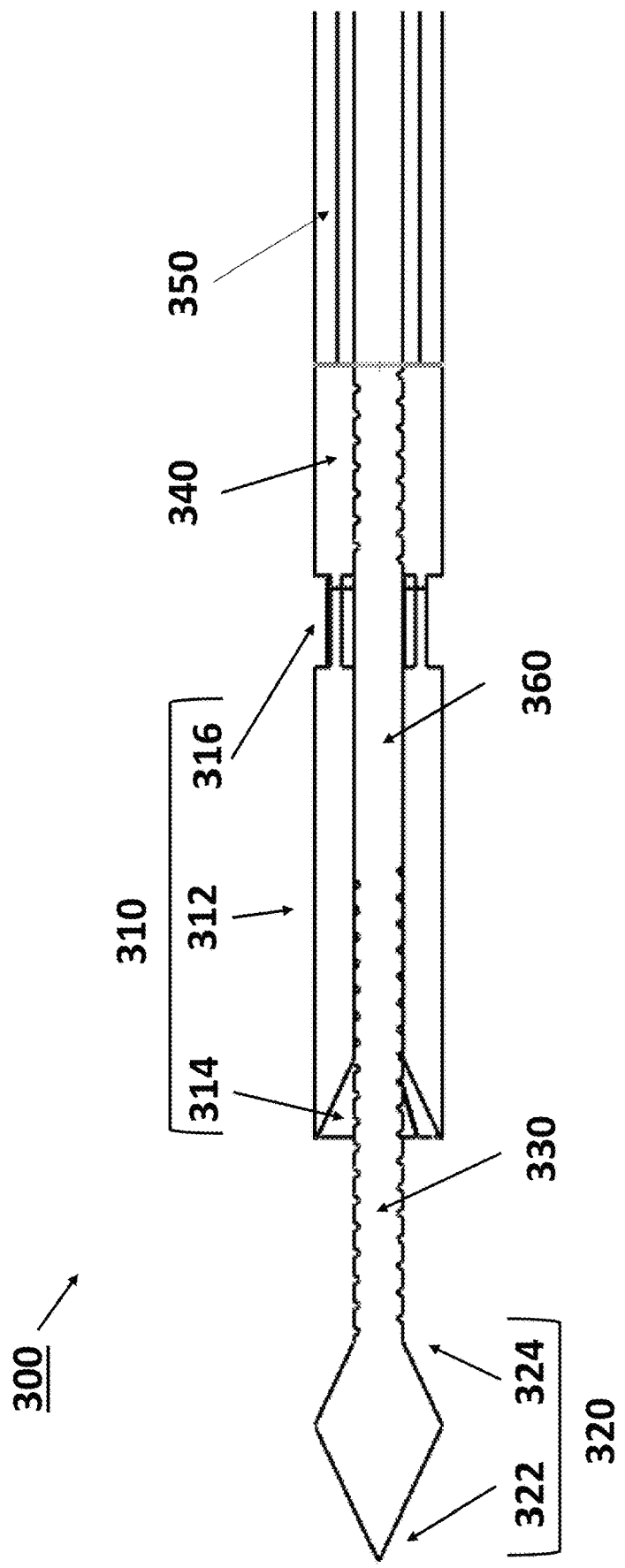
FIG. 3 illustrates an internal side view of one embodiment of the distal end of the device including the dilator head and body with the dilator petal assembly in the closed position.

FIG. 3 illustrates an internal cross-sectional view of one embodiment of the distal end of the device 300 with the dilator petal assembly 301 in the closed position. The distal end of a guiding rod 360 extends from the proximal end of the internal bolt 330. The guiding rod 360 is encased within the outer housing 350.

From this cross-section view of the device 300, the tabs 316 attach the dilator petals 312 to the nut 340. When the dilator petal assembly 310 is in the closed position, the dilator petal tips 314 allow the dilator petal assembly 310 to sit in line with the insertion tips 320 while the tabs 316 sit in line with the nut 340. The entire distal end of the device 300, including the outer housing 350 and the nut 340 are hollow to allow space for the guiding rod 360 and the internal bolt 330. The hollow space allows rotation of the movable, external threaded internal bolt 330 proximally through the stationary, internal threaded nut 340, achieving dilation of the dilator petal assembly 310 while simultaneously keeping the rest of the distal end of the device 300 stationary. For illustrative purposes, the internal bolt 330 is shown in an extended position such that the threads of internal bolt 330 are visible past the petal assembly 310. In some embodiments, the internal bolt 330 never extends past the petal assembly 310.

Figure 4:
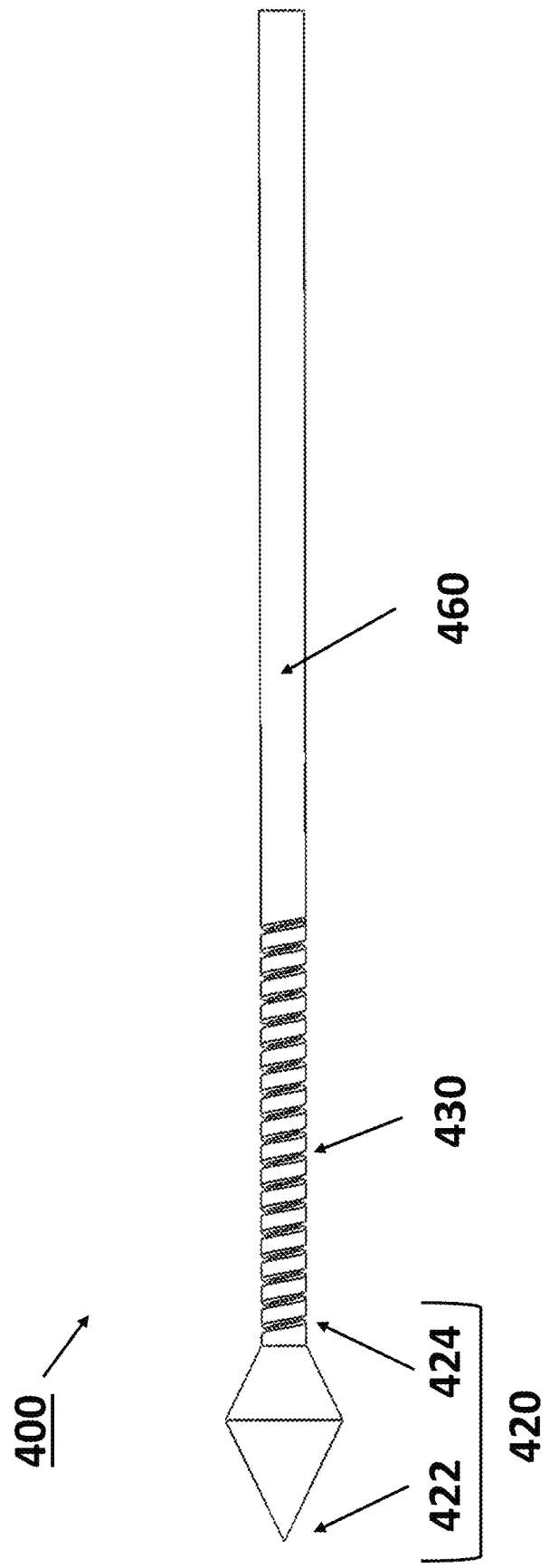
FIG. 4 illustrates an internal side view of one embodiment of the insertion tip with the internal bolt and guiding rod.

FIG. 4 illustrates an external view of one embodiment of the core of the distal end of the device 400. The insertion tip 420 is positioned at the distal end of the device 400. The distal end of the internal bolt 430 is attached to the insertion tip base 424. The insertion tip 420 acts as the internal bolt head for the internal bolt 430. The distal end of the guiding rod 460 attaches to the proximal end of the internal bolt 430 where the threads of the internal bolt 430 end.

Figure 5:
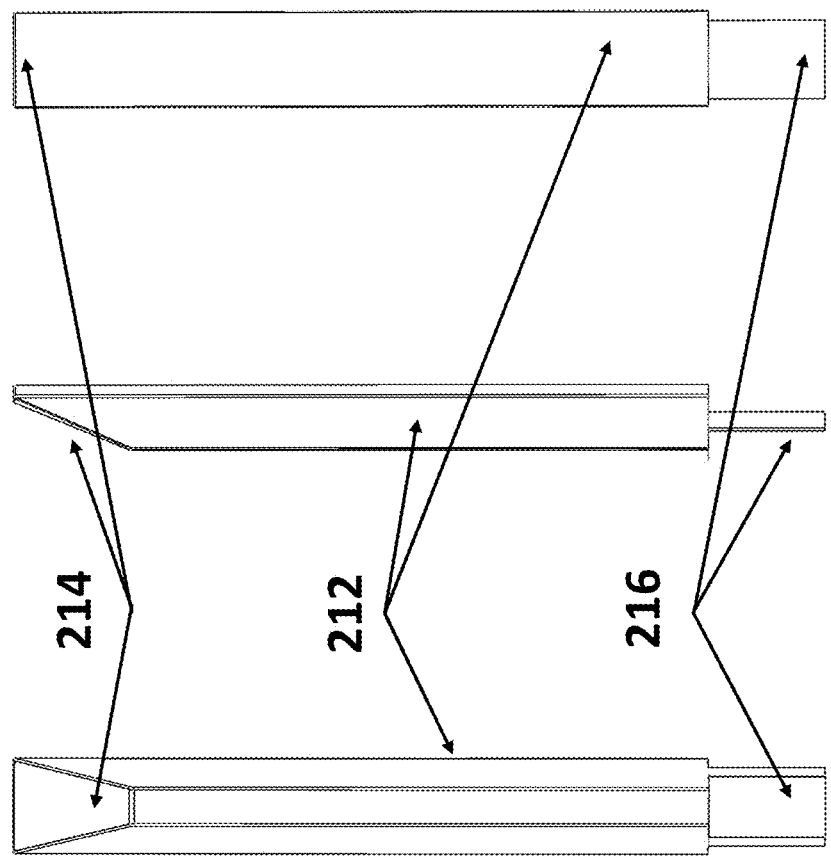
FIGS. 5A-5C illustrate various external perspective views of one embodiment of a single dilation petal.

FIG. 5A, FIG. 5B, and FIG. 5C illustrate various perspective views of one embodiment of a single dilator petal 212. Each dilator petal 212 is an identical section of the hollow cylindrical dilator petal assembly (not shown). Each dilator petal 212 has a dilator petal tip 516 at the distal end which has a beveled edge facing the interior of the dilator petal assembly. Each dilator petal 212 also has a tab 214 at the proximal end. The tab 214, indicated by a dramatic decrease in thickness, is used to attach the dilator petal 212 to the nut (not shown).

Figure 6:
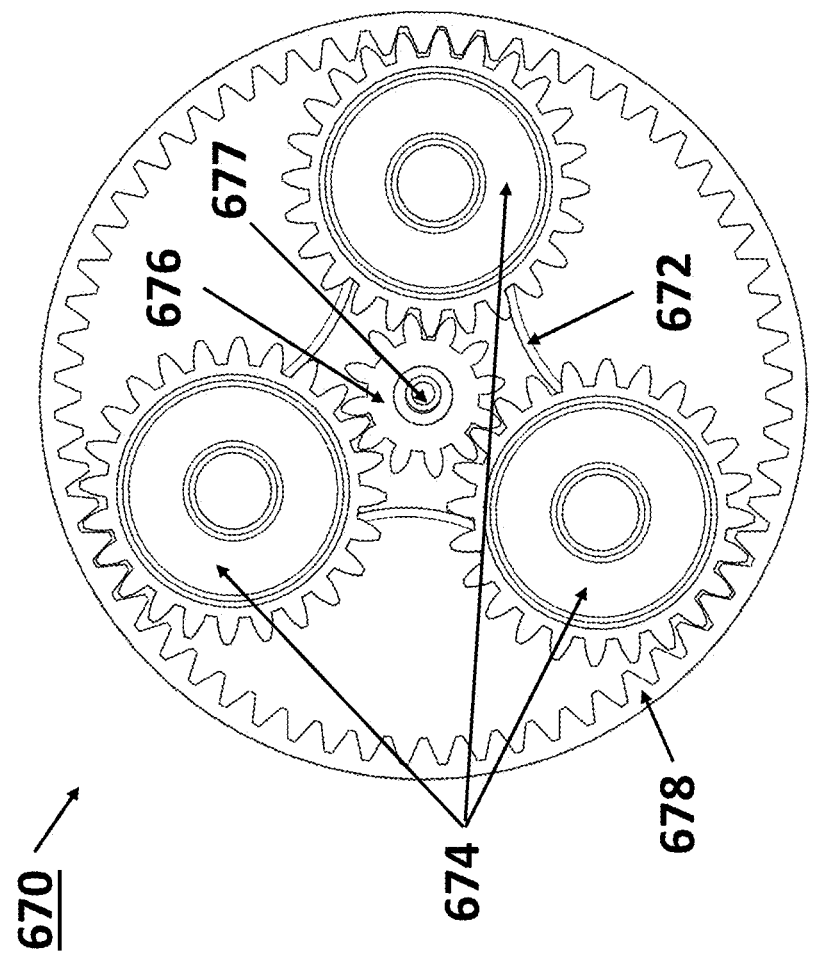
FIG. 6 illustrates an external view of one embodiment of the distal face of the planetary gear system.

FIG. 6 illustrates a front view of one embodiment of the distal face of the planetary gear system 670. The carrier 672 initially moves the planetary gears 674. The three larger planetary gears 674 move the central gear 676. The central gear 676 moves the central gear shaft 677, which extends outward from the front of the central gear 676. The central gear shaft 677 connects the planetary gear system 670 to the dilator body (see FIGS. 1-3). The planetary gears 674 rotate more slowly than the central gear 676, and the planetary gears 674 are fixed within a large ring gear 678 which remains stationary during rotation of the central gear 676 and the planetary gears 674 and resulting dilation.

Figure 7:
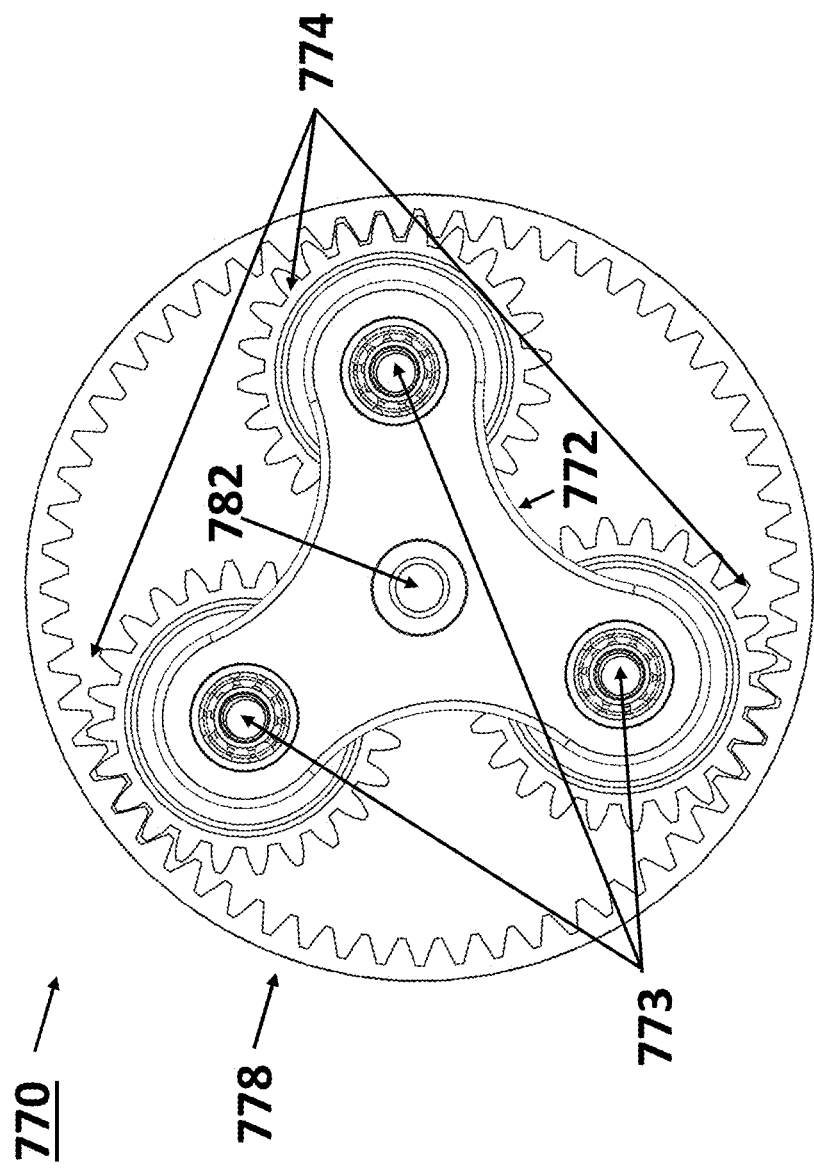
FIG. 7 illustrates an external view of one embodiment of the proximal face of the planetary gear system.

FIG. 7 illustrates a front view of one embodiment of the proximal face of the planetary gear system 770. The carrier 772 rotates the planetary gears 774 within the ring gear 778 using the carrier shafts 773 which extend outward from the back of the planetary gears 774. The carrier shafts 773 connect the planetary gears 774 to the carrier 772. The crank (see FIG. 10) rotates the carrier 772 using the crank shaft 782 which extends outward from the back of the carrier 772. The crank shaft 782 connects the crank (see FIG. 10) to the carrier 772. The planetary gear system 770 with rotates with the rotation of the crank shaft 782.

Figure 8:
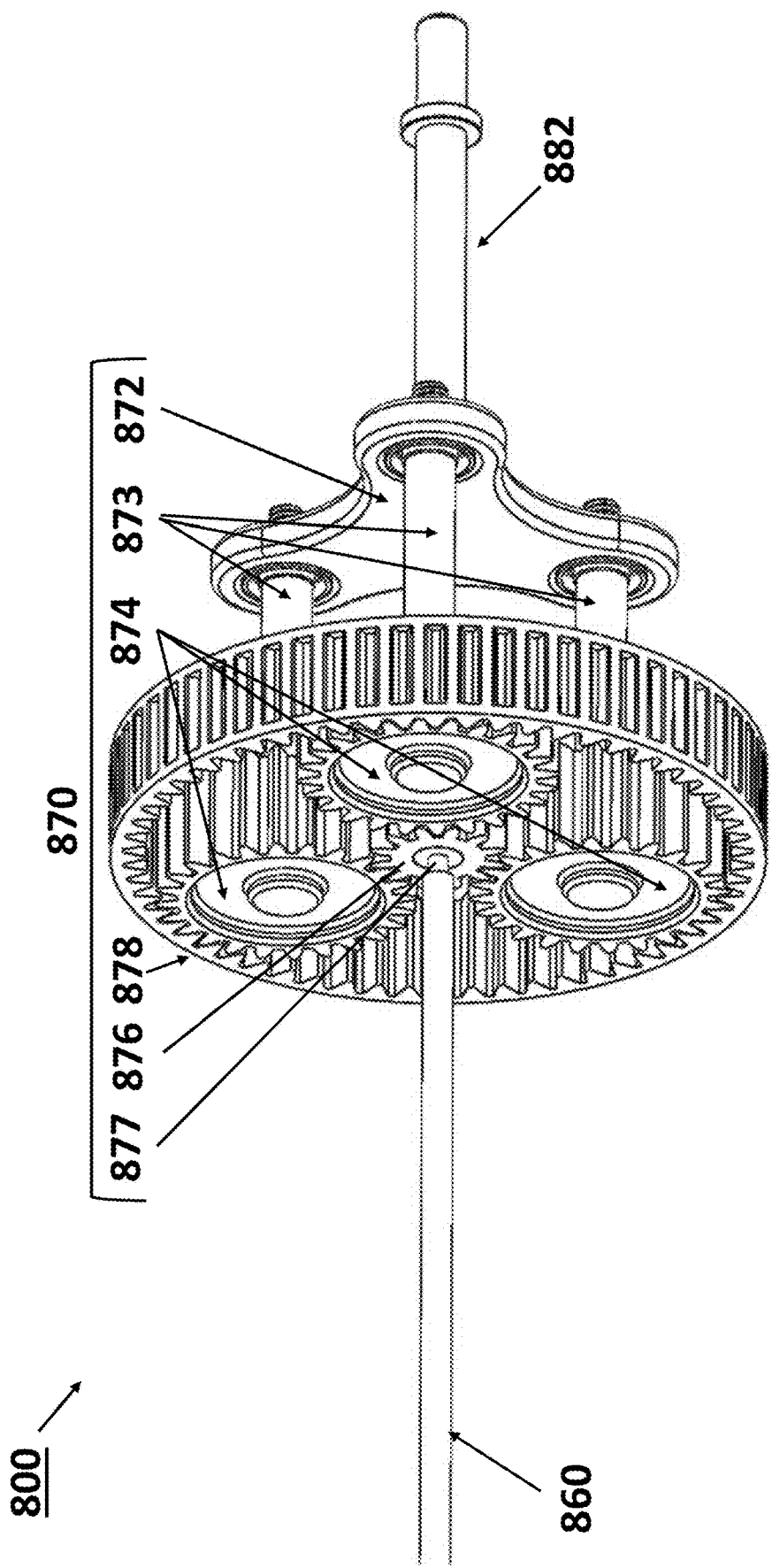
FIG. 8 illustrates an external perspective view of one embodiment of the distal face of the connection of the distal and proximal sections of the device including the guiding rod, the planetary gear system and the crank shaft.

FIG. 8 illustrates a perspective view of one embodiment of the distal face of the device at the transition point 800 between the distal and proximal ends of the device including the guiding rod 860, which may be solid or hollow, the planetary gear system 870, and the crank shaft 882. The crank shaft 882 rotates the carrier 872. The carrier 872 rotates the planetary gears 874 using the carrier shafts 873. The planetary gears within the ring gear 878 rotate the central gear 876. The central gear 876 rotates the central gear shaft 877. The guiding rod 860 is attached to the central gear 876 of by the central gear shaft 877. The central gear shaft 877 is inserted into the proximal end of the guiding rod 860. The guiding rod 860 rotates synchronously with the planetary gear system 870 and the crank shaft 882.

Figure 9:
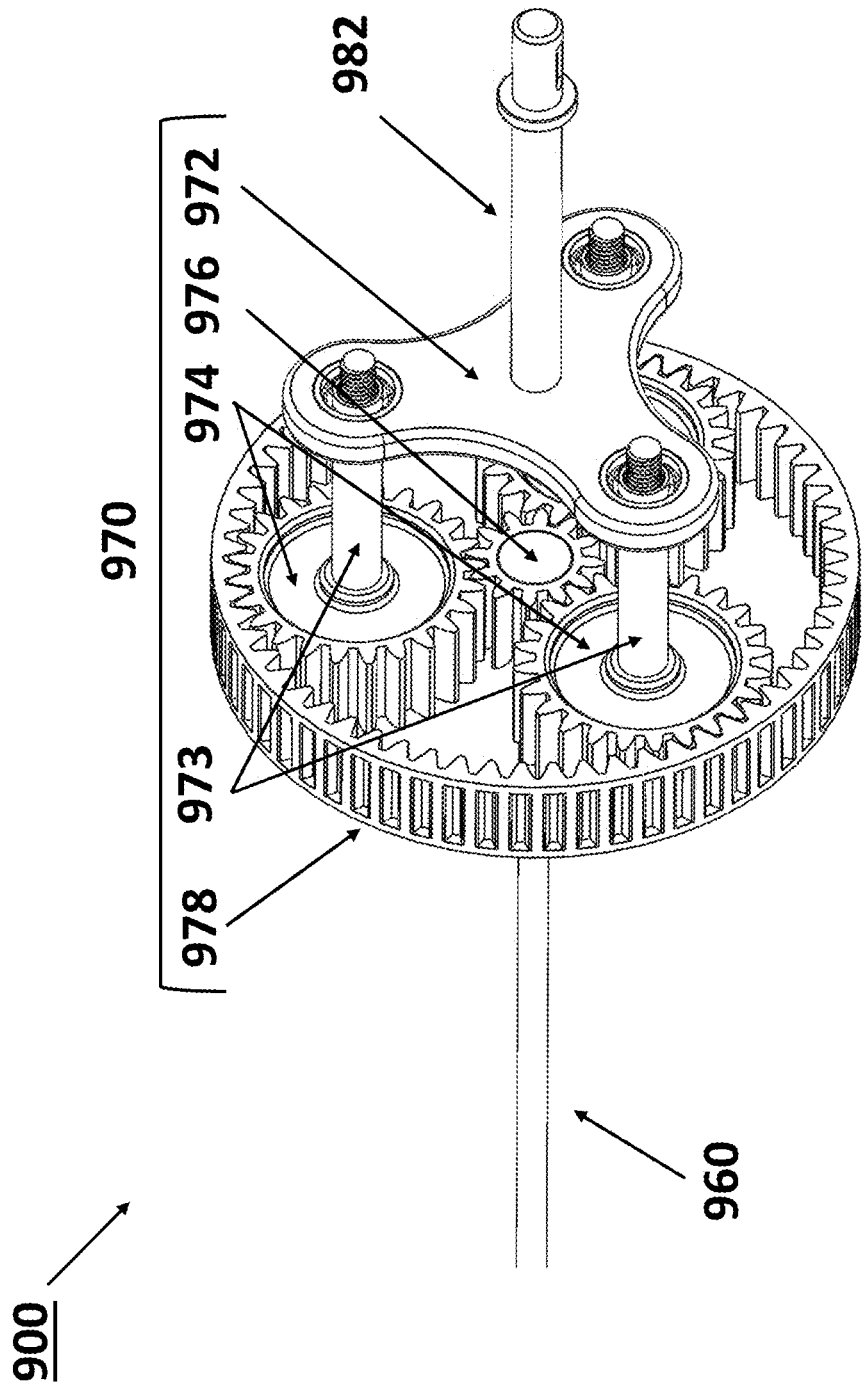
FIG. 9 illustrates an external perspective view of one embodiment of the proximal face of the connection of the distal and proximal sections of the device including the guiding rod, the planetary gear system and the crank shaft.

FIG. 9 illustrates a perspective view of one embodiment of the proximal face of the device at the transition point 900 between the distal and proximal ends of the device including the guiding rod 960, the planetary gear system 970, and the crank shaft 982. The carrier shafts 973 connect the planetary gears 974 to the carrier 972. The crank (see FIG. 10) rotates the carrier 972 using the crank shaft 982 which extends outward from the back of the carrier 972. The crank shaft 982 connects the crank (see FIG. 10) to the carrier 972. The carrier 972 rotates the planetary gears 974 using the carrier shafts 973. The planetary gears within the ring gear 978 rotate the central gear 976. The central gear 976 rotates the central gear shaft (see FIG. 8). The guiding rod 960 is attached to the central gear 976 of by the central gear shaft (see FIG. 8). The central gear shaft (see FIG. 8) is inserted into the proximal end of the guiding rod 960 (see FIG. 8). The guiding rod 960 rotates synchronously with the planetary gear system 970 and crank shaft 982.

Figure 10:
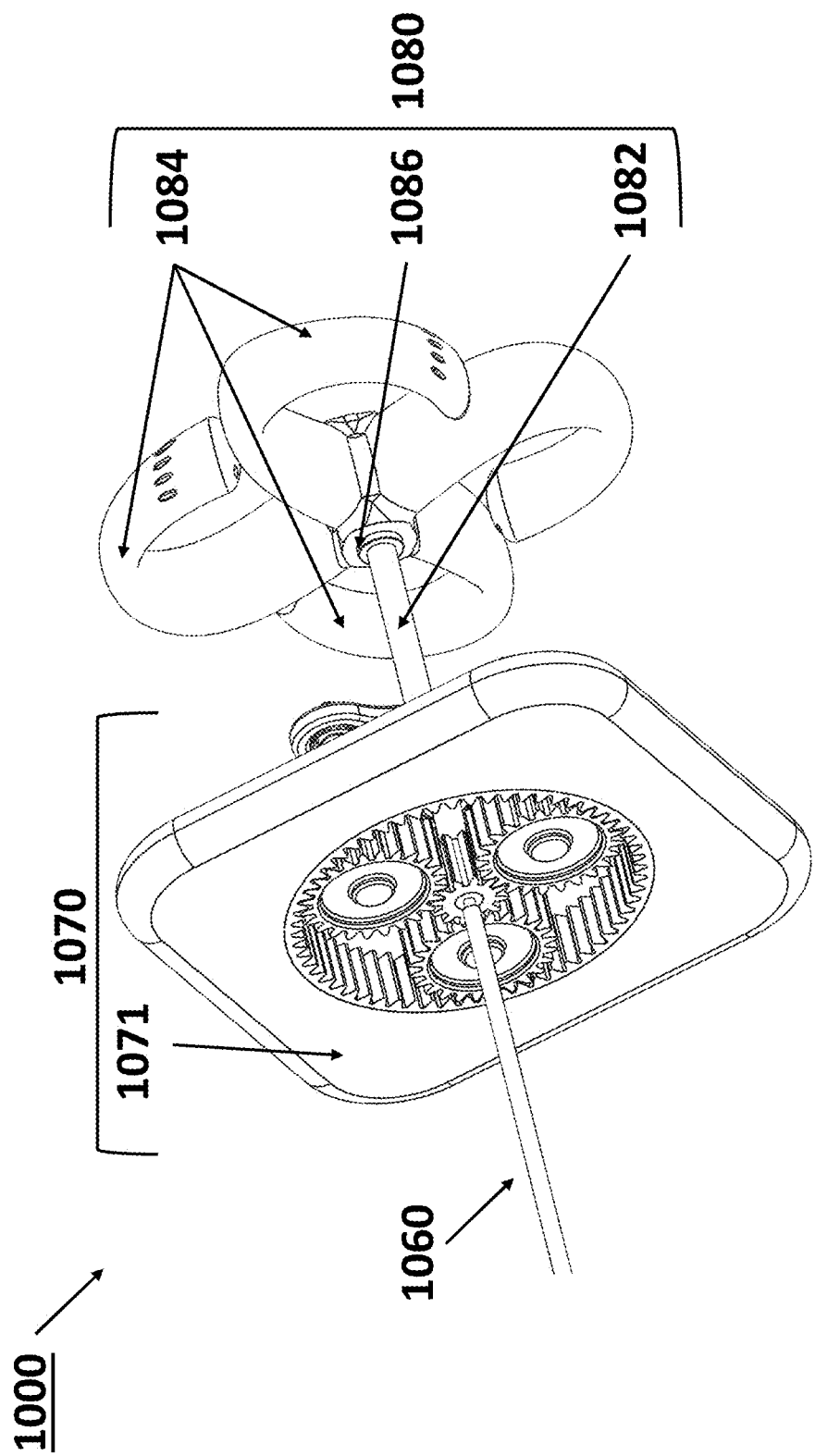
FIG. 10 illustrates an external perspective view of one embodiment of the proximal end of the device including the planetary gear system and the crank.

FIG. 10 illustrates a perspective view of one embodiment of the proximal end of the device 1000 including the guiding rod 1060, the planetary gear system 1070, and the crank 1080. To allow for increased range of motion and stability, the handheld support base 1071 surrounds the interior of the planetary gear system 1070. The planetary gear support base 1071 may easily be held and gripped tightly by the surgeon while rotating the crank handle 1084. The crank 1080 is adhered at its base 1086 to the crank shaft 1082, which attaches the crank 1080 to the planetary gear system 1070. The guiding rod 1060 rotates synchronously with the planetary gear system 1070 and the crank 1080.

Figure 11:
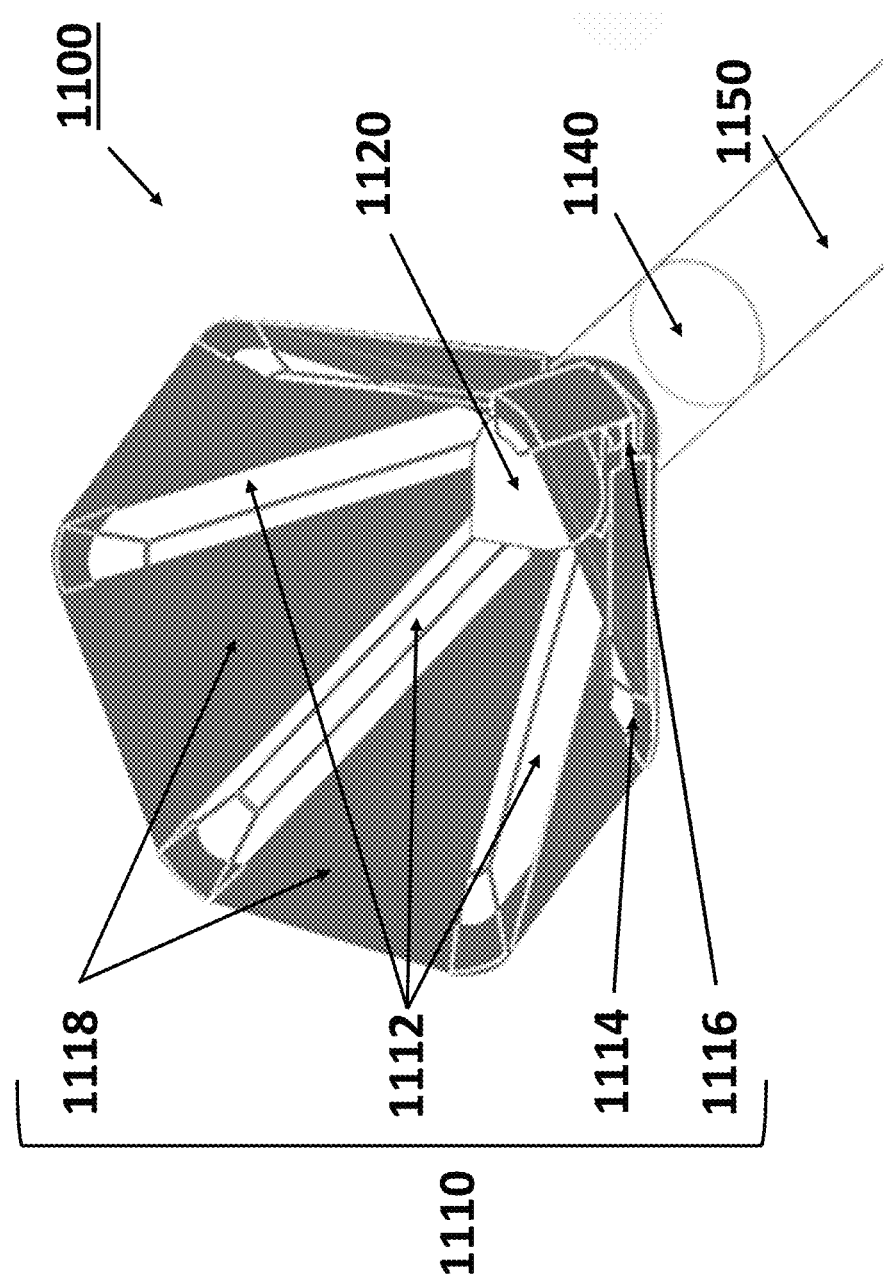
FIG. 11 illustrates an external perspective view of one embodiment of the distal end of the device including the dilator head and body with the dilator petal assembly in the open position and disposed within the interior cavity of a stretchable sleeve.

FIG. 11 illustrates an external view of one embodiment of the distal end of the device 1100 with the dilator petal assembly 1110 in the open position. The stretchable sleeve 1118 extends from the dilator petal tips 1114 to the tabs 1116. The sleeve 1118 does not extend beyond the dilator petal assembly 1110 to encase the nut 1140 or the outer housing 1150. The sleeve 1118 also does not encase the insertion tip 1120. As the dilator petal assembly 1110 opens, the dilator petals 1112 spread radially outward by bending or flexing at the tabs 1116 away from the insertion tip 1120. With the dilator petal assembly 1110 in the fully open position, the dilator petal tips 214 are spread radially outward from the nut 240 to a precise maximum dilation diameter. The sleeve 1118 stretches to conform to the diameter of the dilator assembly in the open position.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A device for dilation of a surgical path, comprising:
a dilator head positioned at the distal end of the device, comprising:
an insertion tip positioned at the distal end of the dilator head, wherein the insertion tip is configured to create and/or expand a surgical path in an individual in need; and
a dilator petal assembly positioned at the proximal end of the insertion tip, wherein the dilator petal assembly comprises two or more dilator petals; and
a dilator body connected to the proximal end of the dilator head;
wherein the device is configured to extend the dilator head in the closed state into the surgical path, wherein the device is configured to transition the dilator head into the open state by opening the dilator petal assembly radially outward from the dilator head,
wherein the device is configured to dilate the diameter of the surgical path by retracting the dilator head in the open state from the surgical path, and
wherein the insertion tip flares out from a conical point at the distal end of the insertion tip to a maximum diameter before tapering to a flat edge at the proximal end of the insertion tip.

2. The device of claim 1, wherein the maximum diameter of the insertion tip is about 5 mm.

3. The device of claim 1, wherein the dilator head further comprises:
a movable, threaded internal bolt connected to the insertion tip, wherein the distal end of the internal bolt is attached to the proximal end of the insertion tip; and
a stationary, internal threaded nut threaded onto a portion of the internal bolt, wherein the internal bolt is configured to rotate, and wherein the internal bolt is configured to move continuously distally or proximally through the nut based on the rotation of the internal bolt.

4. The device of claim 3, wherein the dilator petal assembly is a hollow cylindrical assembly, wherein each of the two or more dilator petals is an equal, non-overlapping sector of the hollow cylindrical assembly, wherein the base of the hollow cylindrical assembly extends distally from the nut, and wherein the longitudinal axes of the two or more dilator petals are substantially parallel to the longitudinal axis of the dilator head when the dilator head is in the closed position.

5. The device of claim 3, wherein the proximal end of each dilator petal comprises a hinged or flexible tab, wherein the tab of each dilator petal is attached to the distal end of the nut, and wherein the dilator petal assembly is configured to bend or flex each dilator petal at the tab radially outward from the dilator head when the dilator head is in the open position.

6. The device of claim 5, wherein a proximal movement of the internal bolt through the nut is configured to force the insertion tip into the hollow cylindrical interior of the dilator petal assembly, and wherein the force of the insertion tip is configured to transition the dilator head into the open state by opening the dilator petal assembly radially outward from the dilator head based on bending or flexing of the two or more dilator petals at the tab of each dilator petal.

7. The device of claim 6, wherein the extent of the proximal movement of the internal bolt through the nut determines the dilation diameter of the dilator petal assembly, and wherein the dilation diameter of the dilator petal assembly determines the dilation diameter of the surgical path.

8. The device of claim 3, wherein the distal end of the nut comprises two or more slots, and wherein the tab of each dilator petal is bonded inside of one of the slots by adhesive, welding, crimping, or other bonding method.

9. The device of claim 3, wherein the tab of each dilator petal is fastened to the distal end of the nut by a screw, a bolt, a rivet, or other mechanical fastener or bonded to the distal end of the nut by adhesive, welding, crimping, or other bonding method.

10. The device of claim 3, wherein each dilator petal comprises a beveled edge angled toward the hollow cylindrical interior of the dilator petal assembly, wherein the beveled edges of the dilator petal assembly define an funnel-shaped cavity housing the insertion tip when the dilator head is in the closed position, wherein the hollow cylindrical interior of the dilator petal assembly houses a portion of the internal bolt, and wherein the cross-section of the hollow cylindrical interior of the dilator petal assembly is smaller than the cross-section of the insertion tip.

11. The device of claim 3, wherein the dilator body comprises:
a guiding rod extending from the internal bolt, wherein the distal end of the guiding rod extends from the proximal end of the internal bolt, wherein the guiding rod is configured to rotate, and wherein the internal bolt is configured to rotate with the guiding rod; and
an outer housing connected to the nut, wherein the distal end of the outer housing is attached to the proximal end of the nut, wherein the outer housing comprises an interior cavity, and wherein the guiding rod is disposed within the interior cavity of the outer housing.

12. The device of claim 11, wherein the guiding rod is a hollow, cylindrical guiding rod or a solid cylindrical guiding rod comprising a proximal cavity.

13. The device of claim 11, wherein the guiding rod is a flexible guiding rod or an inflexible guiding rod.

14. The device of claim 11, wherein the guiding rod is a plastic guiding rod or a metallic guiding rod.

15. The device of claim 11, wherein the guiding rod is at least 10 inches in length.

16. The device of claim 11, wherein the outer housing is a cylindrical outer housing, and wherein the interior cavity of the outer housing is a cylindrical interior cavity.

17. The device of claim 11, wherein the outer housing is a flexible outer housing or an inflexible outer housing.

18. The device of claim 11, wherein the outer housing is a continuous outer housing or a segmented outer housing comprising uniformly-spaced rigid segments connected by intermediate flexible segments.

19. The device of claim 11, wherein the outer housing is a plastic outer housing or a metallic outer housing.

20. The device of claim 11, further comprising:
a guiding rod rotation system, wherein the distal end of the guiding rod rotation system is attached to the proximal end of the guiding rod, wherein the guiding rod rotation system is configured to rotate the guiding rod, and
wherein the device is configured to dilate the dilator petal assembly by synchronous rotation of the guiding rod, and the internal bolt.

21. The device of claim 20, wherein the device is configured to adjustably dilate the dilator petal assembly to a precise dilation diameter by adjusting the extent of synchronous rotation of the guiding rod, and the internal bolt.

22. The device of claim 20, wherein the guiding rod rotation system comprises manual, mechanical, and/or electrical instrumentation configured to rotate the guiding rod.

23. The device of claim 20, wherein a first section of the device comprising the dilator head and dilator body are reversibly attached to a second section of the device comprising the guiding rod rotation system, wherein, prior to surgical use, the first section of the device is configured to attach to the second section of the device, wherein, after surgical use, the first section of the device is configured to detach from the second section of the device, and wherein the attachment and detachment of the first section to and from the second section is based on the attachment and detachment of the guiding rod to and from the guiding rod rotation system.

24. The device of claim 20, wherein the guiding rod rotation system comprises:
a planetary gear system, wherein the distal end of the planetary gear system is attached to the proximal end of the guiding rod, wherein the planetary gear system is configured to rotate, and wherein the guiding rod is configured to rotate with the planetary gear system;
a support base surrounding the planetary gear system; and
a crank positioned at the proximal end of the body, wherein the distal end of the crank is connected to the proximal end of the planetary gear system, wherein the crank is configured to rotate, and wherein the planetary gear system is configured to rotate with the crank,
wherein the device is configured to dilate the dilator petal assembly by synchronous rotation of the crank, the planetary gear system, the guiding rod, and the internal bolt.

25. The device of claim 24, wherein the device is configured to adjustably dilate the dilator petal assembly to a precise dilation diameter by adjusting the extent of synchronous rotation of the crank, the planetary gear system, the guiding rod, and the internal bolt.

26. The device of claim 24, wherein the planetary gear system comprises:
a central gear comprising a central gear shaft extending from the distal side of the central gear, wherein the central gear shaft is attached to the proximal end of the guiding rod, wherein the central gear is configured to rotate the central gear shaft, and wherein the central gear shaft is configured to rotate the guiding rod;
three planetary gears evenly-spaced around the central gear, wherein the teeth of the planetary gears are movably engaged with the teeth of the central gear, and wherein the planetary gears are configured to rotate the central gear;
a stationary ring gear surrounding the planetary gears, wherein the teeth of the planetary gears are movably engaged with the teeth of the ring gear; and
a carrier comprising carrier shafts extending from the carrier to the proximal side of the planetary gears, wherein the carrier is configured to rotate; wherein the carrier shafts are configured to rotate with the carrier, and wherein the carrier shafts are configured to rotate the planetary gears within the ring gear.

27. The device of claim 26, wherein the central gear shaft is inserted into the proximal end of the hollow cylindrical guiding rod or into the proximal cavity of the solid cylindrical guiding rod.

28. The device of claim 26, wherein a first section of the device comprising the dilator head and the dilator body is reversibly attached to a second section of the device comprising the planetary gear system and the crank, wherein, prior to surgical use, a first section of the device comprising is configured to attach to a second section of the device comprising the planetary gear system and the crank, wherein, after surgical use, the first section of the device is configured to detach from the second section of the device, and wherein the attachment and detachment of the first section to and from the second section is based on the attachment and detachment of the guiding rod to and from the central gear shaft.

29. The device of claim 26, wherein the support base is connected to the outer perimeter of the ring gear.

30. The device of claim 24, wherein the crank comprises a crank handle at the proximal end of the crank and a crank shaft connected to the distal end of the crank handle, wherein the distal end of the crank shaft is connected to the proximal end of the carrier, wherein the crank handle is configured to rotate, wherein the crank shaft is configured to rotate with the crank handle, and wherein the carrier is configured to rotate with the crank shaft.

31. The device of claim 30, wherein the crank handle is a valve handle or a spoked wheel handle.

32. The device of claim 24, wherein the crank further comprises a position indicator configured to indicate the precise dilation diameter of the dilator petal assembly based on the extent of rotation of the crank.

33. The device of claim 1, wherein the minimal diameter of dilation of the dilator petal assembly is about 5 millimeters.

34. The device of claim 1, wherein the maximal diameter of dilation of the dilator petal assembly is about 2 centimeters.

35. The device of claim 1, wherein the dilator head further comprises a stretchable sleeve comprising an interior cavity, wherein at least a portion of the dilator petal assembly is disposed within the interior cavity of the sleeve, and wherein the sleeve is configured to stretch to conform to the diameter of the dilator petal assembly when the dilator head is in the open position.

* * * * *